United States Patent [19]

Nohara et al.

[11] 4,267,332
[45] May 12, 1981

[54] 3-(TETRAZOL-5-YL)-1-AZAXANTHONES

[75] Inventors: Akira Nohara, Kyoto; Toshihiro Ishiguro; Kiyoshi Ukawa, both of Osaka, all of Japan

[73] Assignee: Takeda Chemical Industries, Ltd., Osaka, Japan

[21] Appl. No.: 942,925

[22] Filed: Sep. 18, 1978

[30] Foreign Application Priority Data

Sep. 26, 1977 [JP] Japan .................. 52/115817

[51] Int. Cl.³ .................. C07D 273/01; A61K 31/395
[52] U.S. Cl. ........................................ 546/89; 424/256
[58] Field of Search ................................. 546/89

[56] References Cited

U.S. PATENT DOCUMENTS

| 3,931,199 | 1/1976 | Nakanishi et al. | 546/89 |
| 3,931,205 | 1/1976 | Nakanishi et al. | 546/89 |
| 4,085,111 | 4/1978 | Oe et al. | 596/89 |

*Primary Examiner*—Nicholas S. Rizzo
*Assistant Examiner*—D. B. Springer
*Attorney, Agent, or Firm*—Wegner & Bretschneider

[57] ABSTRACT

Novel 3-(tetrazol-5-yl)-1-azaxanthone and its derivatives, which are shown by the following formula

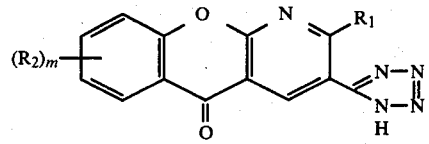

wherein $R_1$ is hydrogen, amino or hydroxyl; $R_2$ is alkyl, alkoxy, halogen, nitro, carboxyl, hydroxyl, butadienylene (—CH=CH—CH=CH—) which forms a benzene ring with any adjacent carbon atoms or amino group which may be unsubstituted or substituted by at least one alkyl; and m is 0, 1 or 2; and their physiologically acceptable salts, are usable as effective medicines for preventing and/or treating allergic diseases.

20 Claims, No Drawings

3-(TETRAZOL-5-YL)-1-AZAXANTHONES

The present invention provides a novel 3-(tetrazol-5-yl)-1-azaxanthone and its derivatives of the formula (I)

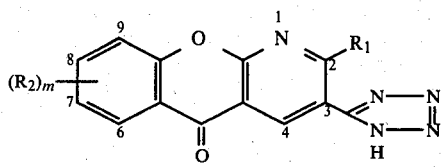

wherein $R_1$ is hydrogen, amino or hydroxyl; $R_2$ is alkyl, alkoxy, halogen, nitro, carboxyl, hydroxyl, butadienylene (—CH=CH—CH=CH—) which forms a benzene ring with any adjacent carbon atoms, or amino group which may be unsubstituted or substituted by at least one alkyl; and m is 0, 1 or 2; and their physiologically acceptable salts, which have excellent pharmacological activities such as antiallergic and bronchodilating activities.

The object compounds of the formula (I) may be produced by reacting a compound of the formula (II)

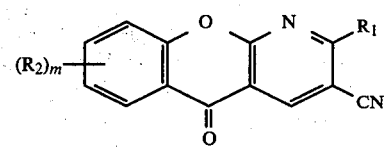

wherein $R_1$, $R_2$ and m have the same meaning as defined above, with hydrazoic acid or a salt thereof.

The substituent(s) designated as $R_2$ in each of the above-mentioned formulae may take any one or two positions of the 6-, 7-, 8- or 9-positions of the azaxanthone ring.

In the formulae (I) and (II), the alkyl group represented by $R_2$ may be any of straight-chain, branched or cyclic alkyl group having 1 to 6 carbon atoms. Typical examples of the alkyl group may be methyl, ethyl, propyl, isopropyl, butyl, isobutyl, sec.-butyl, tert.-butyl, pentyl, hexyl, cyclopentyl and cyclohexyl. Among them, for practical purposes, lower alkyls having 1 to 3 carbon atoms are preferred.

The alkoxy group may for example be that having 1 to 4 carbon atoms, such as methoxy, ethoxy, propoxy, isopropoxy and butoxy.

The halogen may be chlorine, bromine, iodine or fluorine.

The amino group which may be unsubstituted or substituted by at least one alkyl includes amino and mono- or dialkyl substituted ones whose alkyl moiety is that having 1 to 3 carbon atoms, e.g. methylamino, ethylamino, propylamino, isopropylamino, dimethylamino, diethylamino or dipropylamino.

The compound (I) according to this invention can be produced by reacting a compound (II) with hydrazoic acid or a salt thereof. As examples of said salt of hydrazoic acid there may be mentioned the salts of hydrazoic acid with alkali metals (e.g. lithium azide, sodium azide and potassium azide), with alkaline earth metals (e.g. magnesium azide, calcium azide, barium azide and strontium azide), with other metals capable of forming salts with hydrazoic acid (e.g. aluminum azide, tin azide, zinc azide, titanium azide, etc.) and with organic bases such as ammonia and aniline. The salt of hydrazoic acid may be employed alone or in combination with certain other compounds. For example, an alkali metal azide (e.g. sodium azide) may be used together with a Lewis acid (e.g. aluminum chloride, stannic chloride, zinc chloride or titanium chloride) or ammonium chloride. It is likely that, in the reaction system, the alkali metal salt of hydrazoic acid is converted to a different azide corresponding to the cation of the companion compound, namely aluminum azide, tin azide, zinc azide, titanium azide, ammonium azide or the like, and said different azide then reacts with starting compound (II). Of all of said hydrazoic acid, salts thereof and various combinations of said salts with said other compounds, the combination of sodium azide with ammonium chloride is most desirable.

Generally, the reaction is preferably conducted in an organic solvent. As examples of said organic solvent there may be mentioned hydrocarbons such as benzene, toluene and petroleum ether; ethers such as tetrahydrofuran, dioxane, ethyl ether and ethylene glycol dimethyl ether, acetonitrile, dimethylformamide, formamide and dimethylsulfoxide. While temperature, time and other conditions of reaction are not so critical, it is generally advantageous to carry out the reaction at room temperature to about 150° C. for a time from about an hour to about 2 days.

When a salt of hydrazoic acid as such is employed in the reaction, the contemplated compound (I) is obtained in the form of a salt corresponding to the salt of hydrazoic acid employed, this being due to the acidity of the tetrazole ring. This salt, upon treatment with a suitable acid (e.g. a mineral acid such as hydrochloric acid or sulfuric acid), readily transforms itself into the contemplated compound (I) having a free tetrazole ring. Reacting any of the compounds (I) with an organic amine, alkali metal hydroxide, ammonia or other reagent in the routine manner, i.e. under heating in a suitable solvent, yields the corresponding salt of compound (I). As examples of such salt-forming reagents there may be mentioned such organic amines as ethanolamine, diethanolamine, dl-methylephedrine, 1-(3,5-dihydroxyphenyl)-L-isopropylaminoethanol, isoproterenol, dextromethorphan, hetrazan (diethylcarbamazine), diethylamine and triethylamine, such alkali metal hydroxides as sodium hydroxide and potassium hydroxide, and ammonia.

The compounds (I) thus obtained have antiallergic activity and are of value of drugs for the prevention and treatment of such allergic diseases as allergic asthma, allergic dermatitis, and hay fever.

When any of compounds (I) or a salt thereof is used for the prevention or treatment of said allergic diseases, it may be orally administered in such dosage forms as tablets, capsules, powders and solutions, usually at the daily dose level of about 1 to about 500 mg per adult human. It may also be administered by other routes in such dosage forms as injections, aerosol inhalants, ointments and so forth.

The compound of the formula (II), which is a mating material compound in this invention, can be prepared in the following manner.

Thus, a compound of the formula (IV):

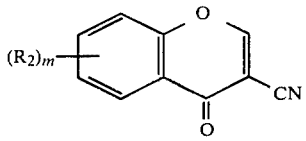

(wherein m and $R_2$ have the same meaning as defined hereinbefore) which can be prepared by the method described in J. Med. Chem. 20, 141(1977) or a method similar thereto, is reacted with water in the presence of a base to prepare a compound of the formula (III):

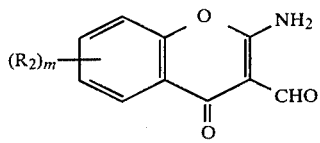

(wherein m and $R_2$ have the same meaning as defined hereinbefore).

As examples of the base used in this reaction, there may be mentioned organic amines such as primary amines (e.g. ethylamine, n-propylamine, n-butylamine, benzylamine and aniline), secondary amines (e.g. dimethylamine, diethylamine, dipropylamine, dibutylamine, morpholine, piperidine and pyrrolidine) and tertiary amines (e.g. triethylamine); heterocyclic bases (e.g. imidazole, 2-methylimidazole, pyridine); and inorganic bases (e.g. aqueous ammonia, ammonium acetate, ammonium carbonate, sodium carbonate and sodium hydrogen carbonate). These bases may be used in a virtually optional proportion from a catalytic amount to a large excess.

Generally, the reaction is conducted preferably in a water-miscible solvent. As examples of such solvent there may be mentioned dimethylformamide, dimethylsulfoxide, hexamethylphosphoric triamide, organic acids such as formic acid, acetic acid and propionic acid and ethers such as tetrahydrofuran and dioxane.

While the temperature, time and other conditions of reaction are not so critical, it is generally advantageous to conduct the reaction at room temperature to about 100° C. for a time from several minutes to about 3 hours.

The compound (III) thus obtained is further reacted with a compound of the formula (V):

$$R_3\text{-CN} \qquad (V)$$

wherein $R_3$ means $HC\equiv C-$, $NC-CH_2-$, $R_4O-COCH_2-$ ($R_4$ is an alkyl radical of 1 to 3 carbon atoms) or $XOC-CH_2-$ (X is halogen) to obtain the starting material compound (II). As examples of the compound (V) in which $R_3$ is $R_4OCOCH_2-$ to be employed in the reaction, there may be mentioned methyl cyanoacetate, ethyl cyanoacetate, propyl cyanoacetate.

The reaction of the compound (III) with the compound (V) in which $R_3$ is $HC\equiv C-$, $NC-CH_2-$ or $R_4OCOCH_2-$ may be conducted in the presence or absence of a base. As examples of said base, there may be mentioned organic amines such as primary amines (e.g. ethylamine, n-propylamine, n-butylamine, benzylamine and aniline), secondary amines (e.g. dimethylamine, diethylamine, dipropylamine, dibutylamine, morpholine, piperidine and pyrrolidine), tertiary amines (e.g. triethylamine) and heterocyclic amines (e.g. imidazole, 2-methylimidazole and pyridine) as well as inorganic bases such as aqueous ammonia, ammonium acetate, ammonium carbonate, sodium carbonate and sodium hydrogen carbonate. These bases may be used in a virtually optional proportion ranging from a catalytic amount to a large excess.

Generally, this reaction is desirably conducted in an organic solvent. As examples of such organic solvent there may be mentioned dimethylformamide, dimethylsulfoxide, formamide, hexamethylphosphoric amide, ethers such as tetrahydrofuran and dioxane, alcohols such as methanol, ethanol, propanol and butanol, esters such as ethyl acetate and methyl propionate, and ketones such as acetone, and methyl ethyl ketone.

While the temperature, time and other conditions of reaction are not so critical, it is generally advantageous to conduct the reaction at room temperature to about 180° C. for a time from several minutes to about 24 hours.

The compound (II) is also produced by reacting a compound of the formula (III) with a compound (V) in which $R_3$ is $XOC-CH_2-$, that is, cyanoacetyl halide in the presence of a substituted formamide. The cyanoacetyl halide employed in this reaction may be cyanoacetyl chloride, cyanoacetyl bromide, cyanoacetyl iodide, cyanoacetyl fluoride or the like. The substituted formamide used in this reaction may be an alkyl or aryl-substituted formamide, such as N,N-dimethylformamide, N,N-diethylformamide, N,N-dipropylformamide, N-methyl-N-ethylformamide, N-methyl-N-phenylformamide, N,N-diphenylformamide or the like. This reaction may be conducted in the presence of such a substituted formamide alone, i.e. using it as the reaction solvent, although the reaction may be carried out, if required, in a solvent mixture of said substituted formamide with an extraneous solvent that will not interfere with the reaction. The solvent just mentioned is preferably one of the common organic solvents such as hydrocarbons (e.g. benzene, toluene, xylene and petroleum ether), ethers (e.g. tetrahydrofuran, dioxane, ethyl ether and ethylene glycol dimethylether), halogenated hydrocarbons (e.g. chloroform, dischloromethane, dichloroethane and tetrachloroethane), esters (e.g. ethyl acetate, methyl acetate and butyl acetate), acetonitrile and dimethylsulfoxide. The proportion of cyanoacetyl halide used in the production of compound (II) is normally in the range of about 1 to 10 molar equivalents based on starting compound (III). While the temperature, time and other conditions of reaction are not particularly critical, the reaction is normally carried out at about 20° to about 120° C. for about 30 minutes to about 2 days. The proportion of said substituted formamide is not particularly critical, either. It is, however, used in a proportion of about 2 or more molar equivalents based on starting compound (III).

While the starting compound (II) for this invention can be prepared in the above manner, the compound (II) in which $R_1$ is hydroxyl can also be prepared by reacting the compound (II) wherein $R_1$ is amino with an alkali salt of nitrous acid (e.g. sodium nitrite or potassium nitrite) in an aqueous solution of acid (e.g. acetic acid or hydrochloric acid).

The following reference and working examples are given to further illustrate this invention.

REFERENCE EXAMPLE 1

A mixture of 2 ml of morpholine, 3 ml of dimethylformamide and 10 ml of water was warmed to 60° C.

and, under stirring, 1.71 g of pulverized b 4-oxo-4H-1-benzopyran-3-carbonitrile was added over a period of 5 minutes. The mixture was held at that temperature for another hour, after which the precipitate was recovered by filtration, rinsed with water, recrystallized from acetic acid and washed with chloroform. By the above precedure there were obtained 1.3 g crystals of 2-amino-4-oxo-4H-1-benzopyran-3-carboxaldehyde, m.p. 252°-255° C. (decomp.)

NMR(DMSO-d$_6$)$\delta$: 10.19(1H, s), 9.67(ca 1.5H, br. s), 8.11 (1H, dd, J=2,8 Hz), 7.97-7.80(3H,m)

Elemental analysis, for $C_{10}H_7NO_3$: Calcd: C, 63.49; H, 3.73; N, 7.41. Found: C, 63.59; H, 3.44; N, 7.45.

In the same manner as above, the following compounds were synthesized.

| Starting compound | Product | m.p. (°C.)/ Recrys. solvent |
| --- | --- | --- |
| 6-Methyl-4-oxo-4H-1-benzopyran-3-carbonitrile | 2-Amino-6-methyl-4-oxo-4H-1-benzopyran-3-carboxaldehyde | 282–284 (decomp.) Acetic acid |
| 6-Ethyl-4-oxo-4H-1-benzopyran-3-carbonitrile | 2-Amino-6-ethyl-4-oxo-4H-1-benzopyran-3-carboxaldehyde | 246–249 (decomp.) Acetone |
| 6-Chloro-4-oxo-4H-1-benzopyran-3-carbonitrile | 2-Amino-6-chloro-4-oxo-4H-1-benzopyran-3-carboxaldehyde | 308–310 (decomp.) Acetic acid |
| 6-Methoxy-4-oxo-4H-1-benzopyran-3-carbonitrile | 2-Amino-6-methoxy-4-oxo-4H-1-benzopyran-3-carboxaldehyde | 251–254 (decomp.) Chloroform |
| 6,8-Dimethyl-4-oxo-4H-1-benzopyran-3-carbonitrile | 2-Amino-6,8-dimethyl-4-oxo-4H-1-benzopyran-3-carboxaldehyde | 259–263 (decomp.) Acetic acid |
| 7-Hydroxy-4-oxo-4H-1-benzopyran-3-carbonitrile | 2-Amino-7-hydroxy-4-oxo-4H-1-benzopyran-3-carboxaldehyde | 297–300 (decomp.) Acetic acid |
| 6-Nitro-4-oxo-4H-1-benzopyran-3-carbonitrile | 2-Amino-6-nitro-4-oxo-4H-1-benzopyran-3-carboxaldehyde | 290–293 (decomp.) Formic acid |
| 6-Isopropyl-4-oxo-4H-1-benzopyran-3-carbonitrile | 2-Amino-6-isopropyl-4-oxo-4H-1-benzopyran-3-carboxaldehyde | 206–208 Acetic acid |
| 6-n-Butyl-4-oxo-4H-1-benzopyran-3-carbonitrile | 2-Amino-6-n-butyl-4-oxo-4H-1-benzopyran-3-carboxaldehyde | 220–222 Acetic acid |
| 8-Methoxy-4-oxo-4H-1-benzopyran-3-carbontrile | 2-Amino-8-methoxy-4-oxo-4H-1-benzopyran-3-carboxaldehyde | 235–238 Chloroform |
| 3-Cyano-benzo[f]-chromone | 2-Amino-benzo[f]-chromone-3-carboxaldehyde | 258–260 (decomp. with foaming) Acetic acid |
| 6-Dimethylamino-4-oxo-4H-1-benzopyran-3-carbonitrile | 2-Amino-6-dimethylamino-4-oxo-4H-1-benzopyran-3-carboxaldehyde | 276–280 (decomp.) Chloroform-Methanol |
| 6-tert.-Butyl-4-oxo-4H-1-benzopyran-3-carbonitrile | 2-Amino-6-tert.-butyl-4-oxo-4H-1-benzopyran-3-carboxaldehyde | 204–242 Acetic acid |
| 6-Isopropoxy-4-oxo-4H-1-benzopyran-3-carbonitrile | 2-Amino-6-isopropoxy-4-oxo-4H-1-benzopyran-3-carboxaldehyde | 218–219 Chloroform |

REFERENCE EXAMPLE 2

A mixture of 217 mg of 2-amino-6-ethyl-4-oxo-4H-1-benzopyran-3-carboxaldehyde, 300 mg of malononitrile, 5 ml of ethanol and 0.5 ml of piperidine was stirred under reflux for 15 minutes and, after cooling, the sparingly soluble product was collected by filtration and recrystallized from dimethylformamide. By the above procedure was obtained 160 mg of 2-amino-7-ethyl-1-azaxanthone-3-carbonitrile as colorless needles, m.p. >300° C.

Infrared absorption spectrum (Nujol) cm$^{-1}$: 3325, 3125, 2225, 1660

Nuclear magnetic resonance spectrum (CF$_3$COOD)$\delta$: 9.07(1H, s), 8.16(1H, d, J=2 Hz), 7.88(1H, dd), 7.63 (1H, d, J=9 Hz), 2.92(2H, q, J=7 Hz), 1.39(3H, t, J=7 Hz).

Elemental analysis, for $C_{15}H_{11}N_3O_2$: Calcd: C, 67.91; H, 4.18; N, 15.84. Found: C, 67.75; H, 4.01; N, 16.00.

The following compounds were produced by procedures similar to that described above.

| Starting compound | Product | m.p. (°C.)/ Recrys. solvent |
| --- | --- | --- |
| 2-Amino-4-oxo-4H-1-benzopyran-3-carboxaldehyde | 2-Amino-1-azaxanthone-3-carbonitrile | >300 Dimethylformamide |
| 2-Amino-6-chloro-4-oxo-4H-1-benzopyran-3-carboxaldehyde | 2-Amino-7-chloro-1-azaxanthone-3-carbonitrile | >300 Dimethylformamide |
| 2-Amino-6-dimethylamino-4-oxo-4H-1-benzopyran-3-carboxaldehyde | 2-Amino-7-dimethylamino-1-axaxanthone-3-carbonitrile | >300 Ethanol |
| 2-Amino-6-isopropyl-4-oxo-4H-1-benzopyran-3-carboxaldehyde | 7-Isopropyl-2-amino-3-cyano-1-azaxanthone | >300 Dimethylformamide |
| 2-Amino-6-methyl-4-oxo-4H-1-benzopyran-3-carboxaldehyde | 7-Methyl-2-amino-3-cyano-1-azaxanthone | >300 Dimethylformamide |
| 2-Amino-8-methoxy-4-oxo-4H-1-benzopyran-3-carboxaldehyde | 9-Methoxy-2-amino-3-cyano-1-azaxanthone | >300 Dimethylformamide |
| 2-Amino-benzo[f]-chromone-3-carboxaldehyde | 2-Amino-3-cyano-benzo[h]-1-azaxanthone | >300 Dimethylformamide |

REFERENCE EXAMPLE 3

In 40 ml of dimethylformamide was dissolved 1.82 g of 2-amino-6-ethyl-4-oxo-4H-1-benzopyran-3-carboxaldehyde, followed by the addition of 3.5 g of cyanoacetyl chloride. The mixture was reacted at 60° C. for 3 hours, with constant stirring. The solvent was then distilled off under reduced pressure and the residue was chromatographed on silica gel. The desired product was recovered from the chloroform eluate and recrystallized from acetonitrile. By the above procedure was obtained 1.03 g of 7-ethyl-3-cyano-1-azaxanthone, m.p. 183°–185° C.

The following compounds were produced in the same manner as above.

| Starting compound | Product | m.p. (°C.)/ Recrys. solvent |
| --- | --- | --- |
| 2-Amino-6-methyl-4-oxo-4H-1-benzopyran-3-carboxaldehyde | 7-Methyl-3-cyano-1-azaxanthone | 240–242 Ethanol |
| 2-Amino-4-oxo-4H-1-benzopyran-3-carboxaldehyde | 3-Cyano-1-azaxanthone | 220–226 Ethanol |
| 2-Amino-6-isopropyl-4-oxo-4H-1-benzopyran-3-carboxaldehyde | 7-Isopropyl-3-cyano-1-azaxanthone | 203–205 Ethanol |
| 2-Amino-6-chloro-4-oxo-4H-1-benzopyran-3-carboxaldehyde | 7-Chloro-3-cyanol-1-azaxanthone | 286–288 Dimethylformamide |
| 2-Amino-6,8-dimethyl-4- | 7.9-Dimethyl-3-cyano- | 254–257 |

-continued

| Starting compound | Product | m.p. (°C.)/ Recrys. solvent |
| --- | --- | --- |
| oxo-4H-1-benzopyran-3-carboxaldehyde | 1-azaxanthone | Acetonitrile |
| 2-Amino-6-tert.-butyl-4-oxo-4H-1-benzopyran-3-carboxaldehyde | 7-tert.-Butyl-3-cyano-1-azaxanthone | 247–249 Acetonitrile |

REFERENCE EXAMPLE 4

To 70 ml of dimethylformamide was added 2.2 g of 2-amino-4-oxo-4H-1-benzopyran-3-carboxaldehyde, followed by the addition of 2.5 g of cyanoacetylene. The mixture was heated under stirring at 140° C. for 15 hours and the solvent was then distilled off under reduced pressure. The residue was chromatographed on silica gel and eluted with chloroform and recrystallized from acetonitrile to give 0.83 g of 3-cyano-1-azaxanthone as crystals, m.p. 220°–226° C.

Nuclear magnetic resonance spectrum (DMSO-$d_6$)δ: 7.4–8.4(4H, m), 9.10(1H, d, J=2 Hz), 9.30(1H, d, J=2 Hz).

Elemental analysis, for $C_{13}H_6N_2O_2$: Calcd: C, 70.27; H, 2.72; N, 12.61. Found: C, 70.12; H, 2.55; N, 12.50.

The following compounds were produced by procedures similar to the above.

| Starting compound | Product | m.p. (°C.)/ Recrys. solvent |
| --- | --- | --- |
| 2-Amino-6-methyl-4-oxo-4H-1-benzopyran-3-carboxaldehyde | 7-Methyl-3-cyano-1-azaxanthone | 240–242 Ethyl acetate |
| 2-Amino-6-ethyl-4-oxo-4H-1-benzopyran-3-carboxaldehyde | 7-Ethyl-3-cyano-1-azaxanthone | 183–185 Acetonitrile |
| 2-Amino-6-isopropyl-4-oxo-4H-1-benzopyran-3-carboxaldehyde | 7-Isopropyl-3-cyano-1-azaxanthone | 203–205 Ethanol |
| 2-Amino-6-isopropoxy-4-oxo-4H-1-benzopyran-3-carboxaldehyde | 7-Isopropoxy-3-cyano-1-azaxanthone | 259–261 Chloroform-acetonitrile |
| 2-Amino-6,8-dimethyl-4-oxo-4H-1-benzopyran-3-carboxaldehyde | 7,9-Dimethyl-3-cyano-1-azaxanthone | 254–257 Acetonitrile |
| 2-Amino-8-methoxy-4-oxo-4H-1-benzopyran-3-carboxaldehyde | 9-Methoxy-3-cyano-1-azaxanthone | >300 Dimethylformamide |
| 2-Amino-benzo[f]-chromone-3-carboxyaldehyde | 3-Cyano-benzo[h]-1-azaxanthone | 234–239 Chloroform-Ethanol |

REFERENCE EXAMPLE 5

To a solution of 0.5 g of 7-isopropyl-2-amino-3-cyano-1-azaxanthone in 80 ml of acetic acid was added gradually 1.0 g of sodium nitrite at 70° C. After one hour period, 3 ml of water was added to the mixture which was heated at 70° C. for a further one hour. The solvent was distilled off under reduced pressure and then, to the residue, water was added. The yellow precipitate was collected by filtration, rinsed with water and recrystallized from ethanol to give 7-isopropyl-2-hydroxy-3-cyano-1-azaxanthone as yellow crystals, m.p.>300° C.

Elemental analysis, for $C_{16}H_{12}N_2O_3$: Calcd: C, 68.56; H, 4.32; N, 10.00. Found: C, 68.28; H, 4.34; N, 9.70.

REFERENCE EXAMPLE 6

A mixture of 1.73 g of 2-amino-6-methoxy-4-oxo-4H-1-benzopyran-3-carboxaldehyde, 3.2 ml of ethyl cyanoacetate, 80 ml of ethanol and 1.6 ml of piperidine was refluxed with constant stirring for one hour. To the mixture was added 3.2 ml of ethyl cyanoacetate and 1.6 ml of piperidine and, then, the mixture was further refluxed for 3 hours. After cooling, the precipitate was recovered by filtration and recrystallized from chloroform-ethanol (2:1).

By the above procedure there were obtained 1.91 g of ethyl 2-amino-7-methoxy-1-azaxanthone-3-carboxylate as colourless needles, m.p. 286°–288° C.

On the other hand, the mother liquor obtained by said filtration was concentrated. The resulting precipitate was recovered by filtration and dissolved in chloroform. The chloroform solution was chromatographed on silica gel (14 g) and elution was carried out with chloroform-acetone-formic acid (9:1:0.1) and, then, chloroform-acetone-formic acid (2:1:0.1). The both eluates were combined and then concentrated. The residue was recrystallized from dimethylformamide-ethanol to obtain 75 mg of 2-hydroxy-7-methoxy-1-azaxanthone-3-carbonitrile as white solid, m.p.>300° C.

IR (Nujol)cm$^{-1}$: 2250(CN), 1680, 1640

NMR(CF$_3$CO$_2$D)δ: 9.20(1H, s), 7.90(1H), 7.75(2H,s), 4.10(3H,s)

Elemental analysis for $C_{14}H_8N_2O_4.1/4H_2O$: Calcd: C, 61.76; H, 3.14; N, 10.29. Found: C, 61.76; H, 2.90; N, 10.31.

EXAMPLE 1

In 50 ml of dimethylformamide was dissolved 0.50 g of 7-isopropyl-3-cyano-1-azaxanthone, followed by the addition of 0.362 g of sodium azide and 0.282 g of ammonium chloride. The reaction was carried out at 120° C. for 2 hours, with constant stirring. The reaction mixture was then distilled to remove the solvent and 5 ml of water was added to the residue, followed by addition of 5 ml of a 5% solution of sodium nitrite. The mixture was made acidic with 10% HCl and the resulting precipitate was collected, rinsed with water and recrystallized from dimethylformamide. By the above procedure there were obtained 0.31 g crystals of 7-isopropyl-3-(1H-tetrazol-5-yl)-1-azaxanthone. m.p. 275°–277° C. (decomp. with foaming.)

NMR(DMSO-$d_6$)δ: 1.30(6H,d,J=7), 3.00(1H,quintet,J=7), 7.70(1H,d,J=8), 7.90(1H, dd,J$_1$=2, J$_2$=8), 8.03(1H,d,J=2), 9.15(1H,d,J=2), 9.38 (1H,d,J=2).

In the same manner as above, the following compounds were synthesized.

3-(1H-Tetrazol-5-yl)-1-azaxanthone, m.p. >300° C.;
7-Ethyl-3-(1H-tetrazol-5-yl)-1-azaxanthone, m.p. 262°–265° C. (decomp. with foaming);
7-Isopropyl-2-amino-3-(1H-tetrazol-5-yl)-1-azaxanthone, m.p. >300° C.;
7-Isopropyl-2-hydroxy-3-(1H-tetrazol-5-yl)-1-azaxanthone, m.p. >300° C.
7,9-Dimethyl-3-(1H-tetrazol-5-yl)-1-azaxanthone, m.p. 294°–298° C.
7-tert.-Butyl-3-(1H-tetrazol-5-yl)-1-azaxanthone, m.p. 273°–275° C. (decomp.)
7-Isopropoxy-3-(1H-tetrazol-5-yl)-1-azaxanthone, m.p. 271°–272° C. (decomp.)
7-Chloro-3-(1H-tetrazol-5-yl)-1-azaxanthone, m.p. >300° C.

3-(1H-Tetrazol-5-yl)-benzo(h)-1-azaxanthone, m.p. 291°–293° C. (decomp.)

9-Methoxy-3-(1H-tetrazol-5-yl)-1-azaxanthone, m.p. >300° C.

EXAMPLE 2

In 150 ml of ethanol was suspended 2.0 g of 6-chloro-2-aminochromone-3-carboxaldehyde, followed by the addition of 1.3 g of malononitrile and 5 ml of piperidine. The mixture was reacted under reflux for 2 hours. The reaction mixture was then distilled under reduced pressure, whereby fractions boiling at and below 100° C. were distilled off. To the residue was added 50 ml of dimethylformamide, followed by the addition of 0.5 g of sodium azide and 0.4 g of ammonium chloride. The reaction was carried out with stirring at 140° C. for 2 hours, at the end of which time the solvent was distilled off under reduced pressure. The residue was diluted with water, treated with 6 ml of 10% sodium nitrite and made acidic with 10% hydrochloric acid. The resultant precipitate was recovered by filtration, rinsed with water and recrystallized from dimethylformamide. By the above procedure there were obtained crystals of 7-chloro-2-amino-3-(1H-tetrazol-5-yl)-1-azaxanthone, m.p. >300° C.

In the same manner as above, the following compounds were synthesized.

7-Nitro-2-amino-3-(1H-tetrazol-5-yl)-1-azaxanthone, m.p. >300° C.;

9-Methoxy-2-amino-3-(1H-tetrazol-5-yl)-1-azaxanthone, m.p. >300° C.;

8-Hydroxy-2-amino-3-(1H-tetrazol-5-yl)-1-azaxanthone, m.p. >300° C.;

Benzo(h)-2-amino-3-(1H-tetrazol-5-yl)-1-azaxanthone, m.p. >300° C.;

7-Dimethylamino-2-amino-3-(1H-tetrazol-5-yl)-1-azaxanthone, m.p. >300° C.; and 7,9-Dimethyl-2-amino-3-(1H-tetrazol-5-yl)-1-azaxanthone, m.p. >300° C.

EXAMPLE 3

To a solution of 0.163 g of 7-isopropyl-2-amino-3-(1H-tetrazol-5-yl)-1-azaxanthone in 20 ml of methanol was added 0.1 g of diethanolamine and then heated at 60° C. for 10 minutes.

After cooling, the separated crystals were collected and recrystallized from methanol to give 7-isopropyl-2-amino-3-(1H-tetrazole-5-yl)-1-azaxanthone diethanolamine salt as colorless needless, m.p. >300° C.

In the same manner as above, the following compound is synthesized.

7-Isopropyl-3-(1H-tetrazole-5-yl)-1-azaxanthone diethanolamine salt, m.p. 149°–151° C.

EXAMPLE 4

An example of practical recipe in which the compound of this invention is utilized as remedies for an allergic disease is as follows:

| (Tablet) | | |
|---|---|---|
| (1) | 7-isopropyl-3-(1H-tetrazol-5-yl)-1-azaxanthone | 1 mg |
| (2) | lactose | 35 mg |
| (3) | corn starch | 169 mg |
| (4) | microcrystalline cellulose | 30 mg |
| (5) | magnesium stearate | 5 mg |
| | | 240 mg |

| (Tablet) -continued | |
|---|---|
| | per tablet |

(1), (2), (3), ⅔ quantity of (4) and half quantity of (5) are throughly mixed, and then the mixture is granulated. Remaining ⅓ quantity of (4) and half of (5) are added to the granules and compressed into tablets. Thus prepared tablets can further be coated with a suitable coating agent, e.g. sugar.

Experiment

According to the biological method hereinafter described, fifty percent inhibitory effect of the drug, i.e., 7-isopropyl-3-(1H-tetrazol-5-yl)-1-azaxanthone, which was produced in the same manner as that of Example 1, on 72 hours passive cutaneous anaphylaxis (PCA) by oral administration was tested in Male Sprague-Dawley rats.

The 50% inhibitory dose on the 72-h PCA in rats was 0.15 mg/kg.

Method

Nine male Sprague-Dawley rats, 8 weeks old weighing 220–320 g, were used. Rat antiserum containing IgE antibody was prepared according to the method of Mota (Life Sci., 2, 917, 1963). In brief, the animals were sensitized by injecting intramuscularly into each hind limb 1 mg of egg albumin in a 1 ml saline solution divided equally, and intraperitoneally a 1 ml suspension of $2 \times 10^{10}$ killed *Bordetella pertussis*. Serum collected from each animal 12 days after sensitization was pooled and frozen until use. Homologous rat passive cutaneous anaphylaxis (PCA) was elicited as follows. Four 0.05 ml aliquots of serum diluted 4-fold with saline were injected intradermally into the shaved dorsal skin of the rat under ether anesthesia. After a 72 hours latent period, the rat was challenged with an intravenous injection of 1 ml of saline containing 5 mg of egg albumin and 10 mg of Evans blue. Animals were sacrificed by bleeding 30 minutes after the antigen challenge and the skin was exfoliated and the intensity of PCA reaction was evaluated by measuring the longest diameter of the wheal stained with dye and the area expressed in terms of $mm^2$. The antisera containing IgE showed PCA titers of 1:16.

Effect of the drug was evaluated with the dose giving 50% inhibition which was calculated graphically from the dose-inhibition relationship.

The drug suspended in 5% gum arabicum was administered orally 5 minutes before the antigen challenge.

What we claim is:

1. A compound of the formula:

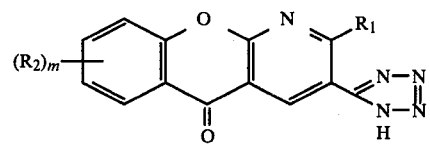

wherein $R_1$ is hydrogen, amino or hydroxyl;

$R_2$ is $C_{1-6}$alkyl, $C_{1-4}$alkoxy, halogen, nitro, carboxyl, hydroxyl, butadienylene attached to any two adjacent carbon atoms, amino, $C_{1-3}$alkylamino or bis($C_{1-3}$alkyl)amino; and m is 0, 1 or 2 or its physiologically acceptable salt.

2. A compound as claimed in claim 1, wherein m is 0.

3. A compound as claimed in claim 1, wherein m is 1.

4. A compound as claimed in claim 1, wherein m is 2.

5. A compound as claimed in claim 1, wherein $R_1$ is hydrogen.

6. A compound as claimed in claim 1, wherein $R_1$ is amino.

7. A compound as claimed in claim 1, wherein $R_1$ is hydroxyl.

8. A compound as claimed in claim 1, wherein $R_2$ is alkyl having 1 to 6 carbon atoms.

9. A compound as claimed in claim 1, wherein $R_2$ is alkoxy.

10. A compound as claimed in claim 1, wherein $R_2$ is halogen.

11. A compound as claimed in claim 1, wherein $R_2$ is butadienylene (—CH=CH—CH=CH—) which forms a benzene ring with any adjacent carbon atoms.

12. A compound as claimed in claim 2, wherein the compound is 3-(1H-tetrazol-5-yl)-1-azaxanthone.

13. A compound as claimed in claim 1, wherein the compound is 7-ethyl-3-(1H-tetrazol-5-yl)-1-azaxanthone.

14. A compound as claimed in claim 1, wherein the compound is 7-isopropyl-3-(1H-tetrazol-5-yl)-1-azaxanthone.

15. A compound as claimed in claim 1, wherein the compound is 7-tert.-butyl-3-(1H-tetrazol-5-yl)-1-azaxanthone.

16. A compound as claimed in claim 1, wherein the compound is 7,9-dimethyl-3-(1H-tetrazol-5-yl)-1-azaxanthone.

17. A compound as claimed in claim 9, wherein the compound is 7-isopropoxy-3-(1H-tetrazol-5-yl)-1-azaxanthone.

18. A compound as claimed in claim 9, wherein the compound is 9-methoxy-3-(1H-tetrazol-5-yl)-1-azaxanthone.

19. A compound as claimed in claim 10, wherein the compound is 7-chloro-3-(1H-tetrazol-5-yl)-1-azaxanthone.

20. A compound as claimed in claim 11, wherein the compound is 3-(1H-tetrazol-5-yl)-benzo(h)-1-azaxanthone.

* * * * *